United States Patent [19]

Harris et al.

[11] Patent Number: 5,405,973

[45] Date of Patent: Apr. 11, 1995

[54] VINYLBENZYL GROUP-CONTAINING SUCCINIC ANHYDRIDE

[75] Inventors: Rodney M. Harris, Chicago; John R. Babjak, Tinley Park; Thomas W. Yokoyama, Chicago; Mohamed D. Shalati, Homewood, all of Ill.

[73] Assignee: The Sherwin-Williams Company, Cleveland, Ohio

[21] Appl. No.: 176,404

[22] Filed: Jan. 3, 1994

[51] Int. Cl.$^6$ ............................................. C07D 307/60
[52] U.S. Cl. ................................... 549/233; 525/108; 525/117; 525/170; 526/271; 526/272
[58] Field of Search ............... 549/233; 526/271, 272

[56] References Cited

U.S. PATENT DOCUMENTS

| | | | |
|---|---|---|---|
| 2,692,270 | 10/1954 | Beavers | 549/233 |
| 2,884,408 | 4/1959 | Phillips et al. | 260/78.3 |
| 3,523,143 | 8/1970 | Kwong | 260/835 |
| 3,594,415 | 7/1971 | Zisman et al. | 260/515 |
| 3,803,254 | 4/1974 | Hattori et al. | 260/669 |
| 3,975,314 | 8/1976 | Smyk et al. | 260/2 |
| 4,026,867 | 5/1977 | Gardiner | 260/46 |
| 4,107,114 | 8/1978 | Nakayama et al. | 260/22 |
| 4,374,235 | 2/1983 | Culbertson et al. | 526/262 |
| 4,599,432 | 7/1986 | Kuroda et al. | 549/255 |
| 4,703,101 | 10/1987 | Singer et al. | 528/87 |
| 4,720,555 | 1/1988 | Nash | 549/252 |
| 4,859,758 | 8/1989 | Shalati et al. | 527/313 |
| 4,871,806 | 10/1989 | Shalati et al. | 525/108 |
| 4,927,868 | 5/1990 | Schimmel et al. | 523/439 |
| 4,946,744 | 8/1990 | Shalati et al. | 428/500 |
| 5,066,742 | 11/1991 | Gupta | 526/216 |
| 5,093,391 | 3/1992 | Barsotti et al. | 523/400 |
| 5,206,295 | 4/1993 | Harper et al. | 525/207 |
| 5,227,243 | 7/1993 | Shalati et al. | 428/457 |

FOREIGN PATENT DOCUMENTS

| | | |
|---|---|---|
| 0723674 | 12/1965 | Canada .......................... 260/479 |
| 46-27530 | 8/1971 | Japan . |
| 48-43191 | 12/1973 | Japan . |
| 57-80408 | 5/1982 | Japan . |
| 62-34247 | 7/1987 | Japan . |
| 1-225964 | 9/1989 | Japan . |

OTHER PUBLICATIONS

Chemical Abstract 101: 131184q Vinyl citrates from citric acid as new monomers (Muisers et al.).
Makromol. Chem., Rapid Commun. 8, 281–281 (1987) *Copolymerization of 1-hexene-3,4-cioic anhydrate and its thermal rearrangement products with styrene.*

*Primary Examiner*—Robert E. Sellers
*Attorney, Agent, or Firm*—Robert E. McDonald; Steven W. Tan; Heidi A. Boehlefeld

[57] ABSTRACT

Anhydride-functional polymerizable monomers having the structure:

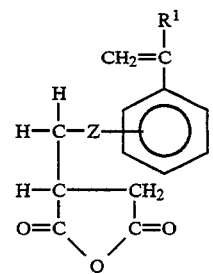

and polymers and reactive compositions prepared from these monomers are disclosed. The reactive compositions are especially useful in primer, topcoat, and in clearcoat/basecoat applications.

6 Claims, No Drawings

VINYLBENZYL GROUP-CONTAINING SUCCINIC ANHYDRIDE

BACKGROUND OF THE INVENTION

1. Field of the Invention

This invention involves novel anhydride-functional polymerizable monomers and polymers and reactive compositions prepared from those monomers. The anhydride-functional monomers have the structure:

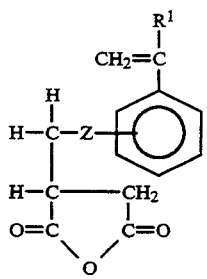

wherein $R^1$ is hydrogen or methyl; and Z is nothing or is a divalent alkyl radical having 1 to about 20 carbon atoms. Preferred divalent alkyl radicals are methylene chains $-(-CH_2-)_n-$ wherein n is 1 to 20.

This invention also relates to anhydride-functional polymers having an average of at least two anhydride groups per molecule and which are obtained by polymerizing, under free radical addition polymerization conditions, (i) the anhydride-functional monomer of this invention; and (ii) optionally, at least one other unsaturated monomer copolymerizable with the anhydride-functional monomer.

The anhydride-functional monomers can be utilized as, for example, nuetralizing agents, or thickeners, or they may be polymerized to provide anhydride-functional polymers. The anhydride-functional polymers are useful as corrosion or scale inhibitors, thickeners, dispersants and as reactive agents and/or crosslinking agents for compounds having functional groups, such as epoxy, hydroxyl or amine groups, which are reactive with anhydride groups. The anhydride-functional monomers and polymers can, therefore, be utilized in a variety of materials such as plastics, fibers, adhesives, paper sizing, inks and, particularly, coating compositions.

This invention also relates to novel reactive compositions which utilize the anhydride-functional polymer. The reactive compositions can be reacted at room temperature or force dried at temperatures ranging up to about 350° F. or higher if desired. When utilized as reactive crosslinking agents for coatings, the anhydride-functional polymers may be utilized in a variety of coating applications, including primers and topcoats as well as clearcoats and/or basecoats in clearcoat/basecoat compositions.

The reactive compositions typically involve the combination of the anhydride-functional polymer with materials reactive with anhydrides such as polyepoxides, polyamines, polyols, etc. One preferred curable coating combination comprises the anhydride-functional polymer and a polyol, preferably a hydroxy-functional polymer, optionally in combination with an epoxide or polyepoxide. Another preferred reactive composition comprises the anhydride-functional polymer, an acid-functional polymer, an epoxide or polyepoxide, and, optionally, a polyol. All of these combinations provide fast reacting, durable coatings which may minimize the toxicity problems which may be associated with other low temperature curing systems. 2. Description of the Prior Art Unsaturated anhydrides, such as maleic anhydride, and copolymers made from maleic anhydride are known in the art. Such anhydride copolymers are heterogeneous with respect to the distribution of anhydride groups along the backbone of the polymer due to the abnormal copolymerization behavior of maleic anhydride with other monomers, and the acid groups generated from opening these anhydrides by reaction with hydroxyl or amine groups are not highly reactive for further cure reactions, e.g. with epoxy groups, due to steric hindrance arising from the proximity of the anhydride ring to the polymer backbone. Such anhydride-functional polymers are also relatively viscous and are difficult to utilize in combination with low levels of solvent. Additionally, such polymers may form dark colored materials when certain base catalysts, such as N-methyl imidazole, are used to accelerate a subsequent reaction of the polyanhydride with reactive materials such as hydroxy-functional compounds.

Coating compositions comprising polyanhydrides and hydroxy-functional compounds are known in the art. For example, U.S. Pat. No. 4,946,744 teaches clearcoat/basecoat combinations involving (i) a polyanhydride, for example, such as that prepared by copolymerization of maleic anhydride with (meth)acrylic monomers, and (ii) a polyol. U.S. Pat. No. 5,227,243 teaches curable compositions comprising a polyanhydride, a polyol and an epoxy-functional compound. U.S. Pat. No. 4,871,806 teaches curable compositions comprising a polyanhydride, a polyacid, a polyol and an epoxy-functional compound. U.S. Pat. No. 4,859,758 teaches an acid-functional cellulose ester based polymer which could be used in combination with a polyanhydride and a polyepoxide. U.S. Pat. No. 4,927,868 teaches copolymers of α-olefins and unsaturated anhydrides which could be used with a polyepoxide and, preferably, a polyacid. U.S. Pat. No. 4,374,235 teaches anhydride-functional polymers prepared by the polymerization of an alkenyl succinic anhydride and a vinyl monomer. The prior art has not, however, taught polymers obtained by the polymerization of the novel anhydride monomers of this invention.

BRIEF SUMMARY OF THE INVENTION

This invention involves polymerizable unsaturated monomers having pendent anhydride functionality. These versatile monomers have a variety of potential applications due to their combination of reactive sites. Either the anhydride or the unsaturation functionality could be reacted first, followed, if desired, by subsequent reaction of the other functionality. For example, the anhydride group could be reacted with hydroxyl groups on an alcohol or polyol to provide a product having one or more pendent, polymerizable unsaturation sites. Such a product could be subsequently polymerized, either with or without additional copolymerizable monomers such as styrene or (meth)acrylic monomers, by peroxide initiation or by exposure to high energy radiation such as electron beam or ultraviolet light. The anhydride-functional monomer could also be hydrolyzed to produce a diacid-functional monomer.

A particularly preferred use for the monomers of this invention involves their use in polymers derived by polymerizing the anhydride through its unsaturation either as a homopolymer or, preferably, in combination with one or more additional copolymerizable monomers. The anhydride-functional polymers can be, if desired, fully or partially hydrolyzed, or ring opened by e.g. half-ester or half-amide reactions, to produce acid-functional polymers, or they can be directly utilized as crosslinking agents for materials having functionality which is reactive with anhydride groups such as epoxy, hydroxyl or amine functionality.

Therefore, this invention also relates to curable compositions which comprise (i) anhydride-functional polymers prepared using the monomers of this invention, and (ii) a compound having an average of at least two functional groups per molecule which are reactive with anhydride groups. A particularly preferred curable composition comprises (i) the anhydride-functional polymer and (ii) a hydroxy-functional compound having an average of at least two hydroxyl groups per molecule, optionally in combination with an epoxide or polyepoxide. Another preferred combination comprises (i) the anhydride-functional polymer, (ii) an acid-functional compound having an average of at least two acid groups per molecule, (iii) an epoxide or polyepoxide, and, optionally, (iv) a hydroxy-functional compound having an average of at least two hydroxyl groups per molecule. Another useful composition comprises (i) the anhydride-functional polymer and (ii) a polyamine compound having an average of at least two primary and/or secondary amine groups per molecule. Another useful composition comprises (i) the anhydride-functional polymer and (ii) a polyepoxide. The term "compound" is used in its broadest sense to include monomers, oligomers and polymers.

Although the curable compositions of this invention can be utilized without solvent in many applications, it is frequently preferred to utilize them in combination with about 5% to about 75% by weight of an inert solvent. It is convenient to provide the curable composition as a multicomponent system which is reactive upon mixing the components. Especially preferred is a two-component system wherein the anhydride-functional polymer and the acid-functional compound, if utilized, are combined in one package and the epoxy-functional compound and/or the hydroxy-functional compound provide a second package. The two packages can then be mixed together to provide the curable composition immediately prior to use.

In one preferred application, this invention also relates to coated substrates having a multilayer decorative and/or protective coating which comprises:
(a) a basecoat comprising a pigmented film-forming polymer; and
(b) a transparent clearcoat comprising a film-forming polymer applied to the surface of the basecoat composition;
wherein the clearcoat and/or the basecoat comprises the curable compositions of this invention. The term "film forming polymer" means any polymeric material that can form a film from evaporation of any carrier or solvent.

Accordingly, one object of this invention is to provide novel unsaturated anhydride-functional monomers and polymers therefrom. Another object is to provide improved curable compositions having excellent reactivity at low temperatures. It is a further object to provide coating compositions which may be utilized as primers, topcoats, or clearcoats and/or basecoats in clearcoat/basecoat compositions. Another object is to provide an improved two-package coating composition wherein one package comprises a novel anhydride-functional polymer and, optionally, an acid-functional compound and the other package comprises an epoxy-functional compound and/or a hydroxy-functional compound. Another object is to provide coatings having excellent reactivity, exterior durability and corrosion resistance. A further object is to provide improved coating compositions which can be cured at room temperature or force dried at elevated temperatures. It is also an object of this invention to provide curable compositions which are relatively low in viscosity and which can be utilized with reduced amounts of volatile organic solvents. These and other objects of the invention will become apparent from the following discussions.

DETAILED DESCRIPTION OF THE INVENTION

The unsaturated anhydride monomers of this invention can be conveniently prepared by the reaction of the anion of a trialkyl-1,1,2-ethanetricarboxylate with a vinyl benzene alkyl halide, followed by hydrolysis of the ester groups to acid groups and subsequent decarboxylation and cyclization to produce the unsaturated anhydride. The vinyl benzene alkylhalide has the general structure:

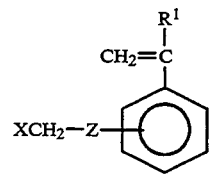

wherein $R^1$ and Z are as defined above and X is a halogen atom. The vinyl benzene alkyl halides of various lengths of Z can be readily prepared by a variety of methods known in the art. For example, Grignard reaction synthesis of the vinyl benzene alkyl halides are representatively set forth in M. L. Hallensleben, *Angew. Makromol. Chem.*, 31,147 (1973), and Montheard, et al. *J. Polym. Sci. Part A., Polym. Chem.*, 27 (8), 2539 (1989). For cost and availability of starting materials, it is especially preferred that Z be nothing or be lower alkyl of 1 to about 4 carbons. Vinyl benzyl chloride, where Z is nothing, $R^1$ is hydrogen, and X is chlorine, is especially preferred.

The production of the unsaturated anhydride monomer is representatively shown below wherein the trialkyl- 1,1,2-ethanetricarboxylate is triethyl- 1,1,2-ethanetricarboxylate, and the vinyl benzene alkyl halide is vinyl benzyl chloride:

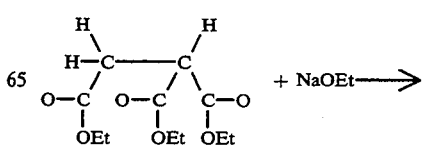

-continued
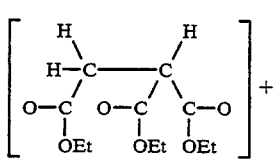
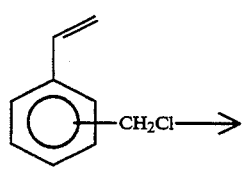
Route A
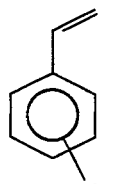 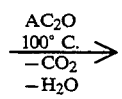
$\xrightarrow{\substack{Ac_2O \\ 100° C. \\ -CO_2 \\ -H_2O}}$
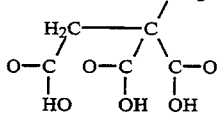
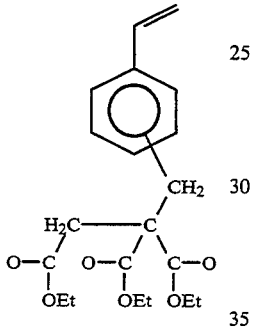
1) KOH H$_2$O EtOH
2) H$^+$
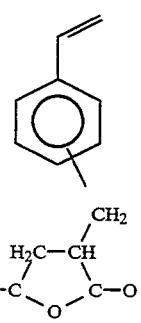
Route B
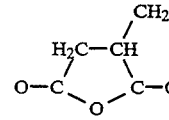
$\xrightarrow{\substack{Neat \\ 125° C.-135° C. \\ vacuum}}$
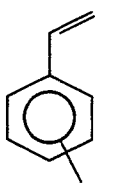 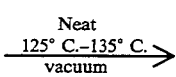
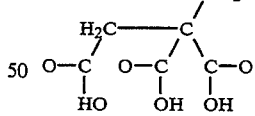
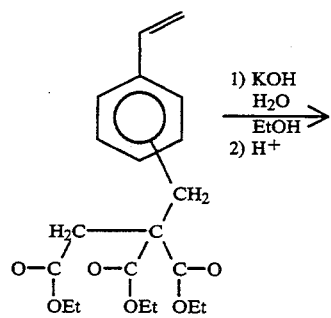
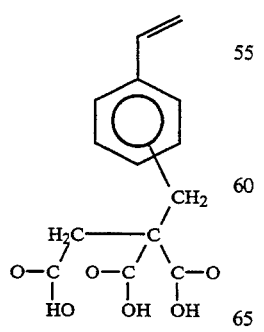
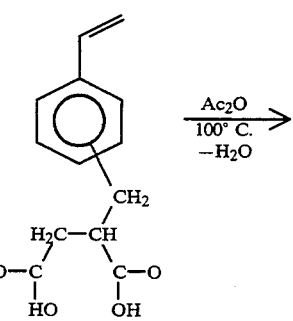
$\xrightarrow{\substack{Ac_2O \\ 100° C. \\ -H_2O}}$ -continued
Route B

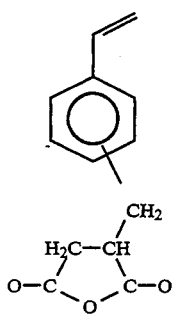

The preparation of the anion of the trialkyl-1,1,2-ethanetricarboxylate is conveniently accomplished by mixing ethanolic sodium ethoxide with the tricarboxylate and refluxing the solution for five to ten minutes. Typically the sodium ethoxide will be present at a level to provide about 0.8 to about 1.1 moles of sodium ethoxide for each mole of tricarboxylate. The anion of the tricarboxylate can then be reacted with the vinyl benzene alkyl halide by mixing the two materials in an approximately 1 to 1 mole ratio and by maintaining the reaction at reflux, in the presence of small amounts (e.g. 500 ppm of the total reaction mixture) of polymerization inhibitors, for 1 to about 3 hours to prepare the vinyl benzene alkyl-1,1,2-ethane tricarboxylate. This tricarboxylate material, in turn, can be hydrolyzed to produce the corresponding tricarboxylic acid by reaction with base, such as sodium hydroxide or potassium hydroxide followed by acidification. Alternatively, the hydrolysis can be conducted by direct reaction of the tricarboxylate with aqueous acid such as aqueous hydrochloric acid. Base hydrolysis is generally preferred and can be readily conducted by admixing an aqueous and/or ethanolic solution of sodium hydroxide or potassium hydroxide and maintaining the reaction mixture at reflux until the reaction is complete (typically 3 to 5 hours). The salt product can be collected by filtration and the tricarboxylic acid is then generated by acidifying an aqueous solution of the salt to a pH less than about 3, typically by the addition of dilute acid such as aqueous hydrochloric acid.

The tricarboxylic acid compound can be converted to the anhydride monomer by several mechanisms. In one approach (Route B) the tricarboxylic acid can be converted to the diacid by heating the tricarboxylic acid at temperatures over 100° C., typically 115° C. to 140° C., until CO2 evolution ceases. The diacid is then reacted with at least an equimolar amount of a reactant, normally a carboxylic acid derivative such as an anhydride or acid chloride, which will produce a better leaving group than the carboxylic acid —OH. For example, the dicarboxylic acid can be reacted with acetic anhydride followed by subsequent elimination of acetic acid upon ring closure. Acetyl chloride, and especially acetic anhydride, are preferred as the carboxylic acid derivatives. The diacid typically would be admixed with acetic anhydride (typically 1 to 5 moles of acetic anhydride to each mole of diacid) and the solution is heated to 80° C. to 100° C. for approximately 1 to 2 hours to provide the anhydride product. Alternatively (as shown in Route A), the tricarboxylic acid can be initially admixed with acetic anhydride (typically there will be 1 to about 10 moles of acetic anhydride for each mole of triacid) and heated to 60° C. to about 120° C., preferably 80° C. to 100° C., for several hours to provide the anhydride product.

The polymerization of the novel monomers of this invention either alone or with other unsaturated copolymerizable monomers, such as (meth)acrylic monomers or styrene, proceeds at excellent yield and provides polymers having excellent reactivity, flexibility and overall performance. The reactivity and flexibility are due, at least in part, to the fact that the anhydride groups are separated by several carbon atoms away from the backbone of the polymer. Furthermore, the pendent succinic anhydride group is monosubstituted, rather than disubstituted as is the case for maleic anhydride copolymers resulting in greater flexibility, lower viscosity and enhanced reactivity. Also, since the styrene-based monomers copolymerize more readily with other unsaturated monomers than does maleic anhydride, a wider practical selection of copolymerizable monomers is available. In many applications, the anhydride-functional polymers of this invention will also provide less color development in the presence of basic catalysts, such as N-methyl imidazole, than will the maleic anhydride based polymers.

1. ANHYDRIDE-FUNCTIONAL POLYMERS

The anhydride-functional polymers which are useful in the practice of this invention will have an average of at least two anhydride groups per molecule and are prepared by polymerizing a monomer mixture comprising the anhydride monomers and normally at least one other copolymerizable monomer under free radical addition polymerization conditions. Polymerizing under free radical addition polymerization conditions means that the monomers are reacted in the presence of a free radical source at a temperature sufficient for polymerization. The monomers which are copolymerized with the anhydride monomer should be free of any functionality which could react with the anhydride group during the polymerization. The anhydride-functional polymers can be conveniently prepared by conventional free radical addition polymerization techniques. Typically the polymerization will be conducted in an inert solvent and in the presence of an initiator, such as a peroxide or azo compound, at temperatures ranging from 35° C. to about 200° C., and especially 75° C. to about 150° C. Representative initiators include di-t-butyl peroxide, cumene hydroperoxide, t-butyl peroctoate and azobis(isobutyronitrile).

The anhydride-functional monomer should generally comprise about 5% to 100% by weight of the monomer mixture used to prepare the anhydride-functional polymer. The remaining 0% to 95% by weight of the monomer mixture will comprise other reactants copolymerizable with the anhydride-functional monomer.

Representative useful copolymerizable (meth)acrylate monomers include methyl acrylate, ethyl acrylate, propyl acrylate, isopropyl acrylate, butyl acrylate, isobutyl acrylate, ethyl hexyl acrylate, amyl acrylate, 3,5,5-trimethylhexyl acrylate, methyl methacrylate, ethyl methacrylate, propyl methacrylate, lauryl methacrylate, isobornyl methacrylate, acrylic acid, methacrylic acid, acrylonitrile, methacrylonitrile, acrylamide and methacrylamide.

Representative monomers which are free of (meth)acrylate functionality and which are copolymerizable with the anhydride-functional monomer include vinyl acetate, vinyl propionate, vinyl butyrate, vinyl isobutyrate, vinyl benzoate, vinyl m-chlorobenzoate, vinyl p-methoxy benzoate, vinyl chloride, styrene, alpha-methyl styrene and maleic anhydride.

An especially preferred anhydride-functional free radical addition polymer comprises the free radical addition polymerization product of (a) 5 to 75, and especially 15 to about 50, weight percent of the anhydride monomer; and (b) 25 to 95, and especially 50 to about 85, weight percent of at least one (meth)acrylic monomer; and, optionally (c) 0 to 70, and especially 0 to about 35 weight percent of at least one unsaturated monomer which is free of (meth)acrylate functionality and is copolymerizable with the anhydride monomer.

2. ACID-FUNCTIONAL COMPOUNDS

The acid-functional compounds which, optionally, can be used in combination with the anhydride-functional polymers of this invention in preparing curable compositions should have an average of at least two carboxylic acid groups per molecule. Although low molecular weight diacids and polyacids such as phthalic acid, succinic acid, adipic acid, azelaic acid, maleic acid, fumaric acid, trimellitic acid and trimesic acid can be utilized in combination with the anhydride-functional polymers in the practice of this invention, it is especially preferred to utilize polymeric acid-functional compounds.

Preferably the acid-functional polymer will have a number average molecular weight of at least about 400. Typical number average molecular weights of the carboxylic acid-functional polymers will range from about 500 to about 30,000. Representative acid-functional polymers include acrylics, polyesters and polymers prepared by the reaction of anhydrides with hydroxyfunctional polymers as discussed more fully below.

2.A. Carboxylic Acid-functional Polymers Prepared by the Half-ester Forming Reaction of Anhydrides and Hydroxy-functional Polymers Especially preferred as acid-functional compounds in the curable compositions of this invention are the carboxylic acid-functional polymers prepared by the half-ester opening of the cyclic anhydride by reaction with a hydroxyl group on the hydroxy-functional polymer to form one ester group and one acid group.

Typically, the hydroxy-functional polymers will have number average molecular weights of at least about 400 and typical number average molecular weights will range from about 400 to about 30,000, and especially 1,000 to about 15,000. Methods of preparing hydroxy-functional polymers are well known in the art and the method of preparation of the hydroxy-functional molecule or polymer which is reacted with the cyclic carboxylic anhydride to produce the optional acid-functional polymer is not critical to the practice of this invention. Representative polymers which can be reacted with anhydrides to produce the acid-functional polymers include the hydroxy-functional polyethers, polyesters, acrylics, polyurethanes, polycaprolactones, etc., as generally discussed in Sections 2.A. 1. through 2.A.5. below.

2.A.1.

Polyether polyols are well known in the art and are conveniently prepared by the reaction of a diol or polyol with the corresponding alkylene oxide. These materials are commercially available and may be prepared by a known process such as, for example, the processes described in *Encyclopedia of Chemical Technology*, Volume 7, pages 257–262, published by Interscience Publishers, Inc., 1951. Representative examples include the polypropylene ether glycols and polyethylene ether glycols such as those marketed as Niax ® Polyols from Union Carbide Corporation.

2.A.2.

Another useful class of hydroxy-functional polymers are those prepared by condensation polymerization reaction techniques as are well known in the art. Representative condensation polymerization reactions include polyesters prepared by the condensation of polyhydric alcohols and polycarboxylic acids or anhydrides, with or without the inclusion of drying oil, semi-drying oil, or non-drying oil fatty acids. By adjusting the stoichiometry of the alcohols and the acids while maintaining an excess of hydroxyl groups, hydroxy-functional polyesters can be readily produced to provide a wide range of desired molecular weights and performance characteristics.

The polyester polyols are derived from one or more aromatic and/or aliphatic polycarboxylic acids, the anhydrides thereof, and one or more aliphatic and/or aromatic polyols. The carboxylic acids include the saturated and unsaturated polycarboxylic acids and the derivatives thereof, such as maleic acid, fumaric acid, succinic acid, adipic acid, azelaic acid, and dicyclopentadiene dicarboxylic acid. The carboxylic acids also include the aromatic polycarboxylic acids, such as phthalic acid, isophthalic acid, terephthalic acid, etc. Anhydrides such as maleic anhydride, phthalic anhydride, trimellitic anhydride, or Nadic Methyl Anhydride (brand name for methylbicyclo[2.2.1]heptene-2,3-dicarboxylic anhydride isomers) can also be used.

Representative saturated and unsaturated polyols which can be reacted in stoichiometric excess with the carboxylic acids to produce hydroxy-functional polyesters include diols such as ethylene glycol, dipropylene glycol, 2,2,4-trimethyl 1,3-pentanediol, neopentyl glycol, 1,2-propanediol, 1,3-propanediol, 1,4-butanediol, 1,3-butanediol, 2,3butanediol, 1,5-pentanediol, 1,6-hexanediol, 2,2-dimethyl-l,3-propanediol, 1,4cyclohexanedimethanol, 1,2-cyclohexanedimethanol, 1,3-cyclohexanedimethanol, 1,4-bis(2-hydroxyethoxy)cyclohexane, trimethylene glycol, tetra methylene glycol, pentamethylene glycol, hexamethylene glycol, decamethylene glycol, diethylene glycol, triethylene glycol, tetraethylene glycol, norbornylene glycol, 1,4-benzenedimethanol, 1,4-benzenediethanol, 2,4-dimethyl-2-ethylenehexane-1,3-diol,2-butene-1,4-diol, and polyols such as trimethylolethane, trimethylolpropane, trimethylolhexane, triethylolpropane, 1,2,4-butanetriol, glycerol, pentaerythritol, dipentaerythritol, etc.

Typically, the reaction between the polyols and the polycarboxylic acids is conducted at about 120° C. to about 200° C. in the presence of an esterification catalyst such as dibutyl tin oxide.

2.A.3.

Additionally, hydroxy-functional polymers can be prepared by the ring opening reaction of epoxides and/or polyepoxides with primary or, preferably, secondary amines or polyamines to produce hydroxy-functional polymers. Representative amines and polyamines include ethanol amine, N-methylethanol amine, dimethyl amine, ethylene diamine, isophorone diamine, etc. Representative polyepoxides include those prepared by condensing a polyhydric alcohol or polyhydric phenol with an epihalohydrin, such as epichlorohydrin, usually under alkaline conditions. Some of these condensation products are available commercially under the designations EPON or DRH from Shell Chemical Company, and methods of preparation are representatively taught in U.S. Pat. Nos. 2,592,560; 2,582,985 and 2,694,694.

2.A.4.

Other useful hydroxy-functional polymers can be prepared by the reaction of an excess of at least one polyol, such as those representatively described in Section 2.A.2 above, with polyisocyanates to produce hydroxy-functional urethanes. Representative polyisocyanates having two or more isocyanate groups per molecule include the aliphatic compounds such as ethylene, trimethylene, tetramethylene, pentamethylene, hexamethylene, 1,2-propylene, 1,2-butylene, 2,3-butylene, 1,3-butylene, ethylidene and butylidene diisocyanates; the cycloalkylene compounds such as 3-isocyanatomethyl-3,5,5-trimethylcyclohexylisocyanate, and the 1,3-cyclopentane, 1,3-cyclohexane, and 1,2-cyclohexane diisocyanates; the aromatic compounds such as m-phenylene, p-phenylene, 4,4'-diphenyl, 1,5-naphthalene and 1,4-naphthalene diisocyanates; the aliphatic-aromatic compounds such as 4,4'-diphenylene methane, 2,4- or 2,6-toluene, or mixtures thereof, 4,4'-toluidine, and 1,4-xylylene diisocyanates; the nuclear substituted aromatic compounds such as dianisidine diisocyanate, 4,4'-diphenylether diisocyanate and chlorodiphenylene diisocyanate; the triisocyanates such as triphenyl methane-4,4',4''-triisocyanate, 1,3,5-triisocyanate benzene and 2,4,6-triisocyanate toluene; and the tetraisocyanates such as 4,4'-diphenyl° dimethyl methane-2,2'-5,5'-tetraisocyanate; the polymerized polyisocyanates such as tolylene diisocyanate dimers and trimers, and other various polyisocyanates containing biuret, urethane, and/or allophanate linkages. The polyisocyanates and the polyols are typically reacted at temperatures of 25° C. to about 150° C. to form the hydroxy-functional polymers.

2.A.5.

Useful hydroxy-functional polymers can also be conveniently prepared by free radical polymerization techniques such as in the production of acrylic resins. The polymers are typically prepared by the addition polymerization of one or more monomers. At least one of the monomers will contain, or can be reacted to produce, a reactive hydroxyl group. Representative hydroxy-functional monomers include 2-hydroxyethyl acrylate, 2-hydroxyethyl methacrylate, 2-hydroxypropyl acrylate, 4-hydroxybutyl acrylate, 4-hydroxybutyl methacrylate, 2-hydroxypropyl methacrylate, 3-hydroxybutyl acrylate, 4-hydroxypentyl acrylate, 2-hydroxyethyl ethacrylate, 3hydroxybutyl methacrylate, 2-hydroxyethyl chloroacrylate, diethylene glycol methacrylate, tetra ethylene glycol acrylate, paravinyl benzyl alcohol, etc. Typically the hydroxyfunctional monomers would be copolymerized with one or more monomers having ethylenic unsaturation such as:

(i) esters of acrylic, methacrylic, crotonic, tiglic, or other unsaturated acids such as: methyl acrylate, ethyl acrylate, propyl acrylate, isopropyl acrylate, butyl acrylate, isobutyl acrylate, ethylhexyl acrylate, amyl acrylate, 3,5,5-trimethylhexyl acrylate, methyl methacrylate, ethyl methacrylate, propyl methacrylate, dimethylaminoethyl methacrylate, isobornyl methacrylate, t-butyl methacrylate, ethyl tiglate, methyl crotonate, ethyl crotonate, etc.;

(ii) vinyl compounds such as vinyl acetate, vinyl propionate, vinyl butyrate, vinyl isobutyrate, vinyl benzoate, vinyl m-chlorobenzoate, vinyl p-methoxybenzoate, vinyl α-chloroacetate, vinyl toluene, vinyl chloride, etc.;

(iii) styrene-based materials such as styrene, α-methyl styrene, α-ethyl styrene, α-bromo styrene, 2,6-dichlorostyrene, etc.;

(iv) allyl compounds such as allyl chloride, allyl acetate, allyl benzoate, allyl methacrylate, etc.;

(v) other copolymerizable unsaturated monomers such as ethylene, acrylonitrile, methacrylonitrile, dimethyl maleate, isopropenyl acetate, isopropenyl isobutyrate, acrylamide, methacrylamide, and dienes such as 1,3-butadiene, etc.

The polymers are conveniently prepared by conventional free radical addition polymerization techniques. Frequently, the polymerization will be catalyzed by conventional initiators known in the art to generate a free radical such as azobis(isobutyronitrile), cumene hydroperoxide, t-butyl perbenzoate, etc. Typically, the acrylic monomers are heated in the presence of the catalyst at temperatures ranging from about 35° C. to about 200° C., and especially 75° C. to 150° C., to effect the polymerization. The molecular weight of the polymer can be controlled, if desired, by the monomer selection, reaction temperature and time, and/or the use of chain transfer agents as is well known in the art.

Especially preferred polymers in the practice of this invention for reaction with the cyclic anhydride to produce the carboxylic acid-functional polymers are hydroxyfunctional polyesters and hydroxy-functional acrylic polymers. An especially preferred hydroxy-functional polymer is the addition polymerization reaction product of (a) 5 to 100, and especially 10 to about 40, weight percent of a hydroxy-functional ethylenically unsaturated monomer and (b) 0 to 95, and especially 60 to about 90, weight percent of at least one other ethylenically unsaturated monomer copolymerizable with the hydroxy-functional monomer.

The cyclic carboxylic acid anhydrides useful in the practice of this invention to produce the carboxylic acid-functional half- ester product by reaction with the hydroxy-functional compound can be any monomeric aliphatic or aromatic cyclic anhydride having one anhydride group per molecule. Representative anhydrides include, phthalic anhydride, 3-nitrophthalic anhydride, 4-nitrophthalic anhydride, 3-flourophthalic anhydride, 4-chlorophthalic anhydride, tetrachlorophthalic anhydride, tetra bromophthalic anhydride, tetrahydrophthalic anhydride, hexahydrophthalic anhydride, methylhexahydrophthalic anhydride, succinic anhydride, dodecenylsuccinic anhydride, octylsuccinic anhydride, maleic anhydride, dichloromaleic anhydride, glutaric anhydride, adipic anhydride, chlorendic anhydride, itaconic anhydride, citraconic anhydride, endomethylenetetrahydrophthalic anhydride, cyclohexane-1,2-dicarboxylic anhydride, 4-cyclohexene- 1,2-dicarboxylic anhydride, 4-methyl-4-cyclohexene- 1,2-dicarboxylic anhydride, 5-norbornene-2,3-dicarboxylic anhydride, 1,4-cyclohexadiene- 1,2-dicarboxylic anhydride, 1,3-cyclopentanedicarboxylic anhydride, diglycolic acid anhydride, etc. Maleic anhydride is especially preferred because of its reactivity and relatively low cost. Other useful anhydrides include those anhydrides having a free carboxyl group in addition to the anhydride group such as trimellitic anhydride, aconitic anhydride, 2,6,7-naphthalene tricarboxylic anhydride, 1,2,4-butane tricarboxylic anhydride, 1,3,4-cyclopentane tricarboxylic anhydride, etc.

The reaction of the hydroxy-functional compound and the cyclic anhydride can be conducted at temperatures ranging up to about 150° C., but should normally be conducted at temperatures less than about 75° C., preferably less than 65° C., and most preferably between about 35° C. to 60° C..The reaction temperature is maintained until the reaction has proceeded to provide the desired amount of half-ester groups on the acid-functional compound. Normally, as a convenient measure of the extent of the reaction, the reaction will be continued until no change in the amount of residual unreacted anhydride can be observed, and will generally involve reacting at least about 70%, and preferably at least 95%, of the available anhydride. If the subsequent end use of the acid-functional polymer can tolerate the remaining free anhydride, if any, no separation or removal of the excess unreacted anhydride is necessary. If the end use of the acid-functional polymer requires that it be free of any unreacted anhydride, the reaction can be continued until substantially all of the anhydride has reacted, or the free anhydride may be removed by vacuum distillation or other techniques well known in the art. The level of anhydride reacted with the hydroxy-functional compound need only be sufficient to provide the final desired acid value of the acid-functional compound. Typically the reaction would be conducted by admixing the polyol and the anhydride at levels to provide at least about 0.3 and normally about 0.7 to 1.0 anhydride groups for each hydroxyl group. By conducting the reaction at temperatures less than about 75° C. the carboxylic acid groups formed as part of the half-ester are not appreciably reactive with the hydroxyl groups themselves and so they do not compete with the ring opening half-ester reaction of the remaining anhydrides. In order to conduct the reaction at these relatively low temperatures, it is preferred to utilize an esterification catalyst. The catalyst should be present in sufficient amount to catalyze the reaction and typically will be present at a level of at least about 0.01%, and normally from about 0.05% to about 3.0%, based upon the weight of the cyclic anhydride. Catalysts which are useful in the esterification reaction of the anhydride with the hydroxy-functional molecule include mineral acids such as hydrochloric acid and sulfuric acid; alkali metal hydroxides such as sodium hydroxide; tin compounds such as stannous octoate, or dibutyltin oxide; aliphatic or aromatic amines, especially tertiary alkyl amines, such as triethylamine; and aromatic heterocyclic amines such as N-methyl imidazole and the like. Especially preferred are N-methyl imidazole and triethylamine. Although the reaction between the hydroxy-functional compound and the anhydride can be conducted in the absence of solvent if the materials are liquid at the reaction temperature, it is normally preferred to conduct the reaction in the presence of an inert solvent such as esters, ketones, ethers or aromatic hydrocarbons. If desired, the acid-functional molecule can be utilized as the solvent solution, or, optionally, all or part of the inert solvent may be removed, e.g. by distillation, after the reaction is completed.

After the reaction is completed, it is frequently desirable to add a low molecular weight alcohol solvent, such as isobutanol or isopropanol, to the acid-functional compound at a level of about 5 to 35 percent by weight to provide stabilization on storage.

2.B. Carboxylic Acid-Functional Polymers Prepared from Unsaturated Acid-Functional Monomers Useful acid-functional polymers can also be conveniently routinely prepared by the free radical addition polymerization of unsaturated acids such as maleic acid, acrylic acid, methacrylic acid, crotonic acid, etc. along with one or more unsaturated monomers. Representative monomers include the esters of unsaturated acids, vinyl compounds, styrene-based materials, allyl compounds and other copolymerizable monomers as representatively taught in Section 2.A.5. of this specification. The monomers which are co-polymerized with the unsaturated acid should be free of any functionality which could react with the acid groups during the polymerization.

2.C. Carboxylic Acid-Functional Polymers Prepared from Polyols and Polyacids Other useful acid-functional polymers include polyester polymers obtained from the reaction of one or more aromatic and/or aliphatic carboxylic acids or their anhydrides and one or more aliphatic and/or aromatic polyols wherein the acid functionality is present in a stoichiometric excess over the hydroxy functionality. Representative carboxylic acids and polyols include those listed in Section 2.A.2. of this specification.

3. EPOXY-FUNCTIONAL COMPOUNDS

The curable coatings of this invention may also incorporate at least one epoxy-functional compound. The epoxy compounds can, if there are sufficient other reactive materials to provide crosslinking, be monoepoxies or, preferably, a polyepoxide having an average of at least two epoxy groups per molecule.

Representative useful monoepoxides include the monoglycidyl ethers of aliphatic or aromatic alcohols such as butyl glycidyl ether, octyl glycidyl ether, nonyl glycidyl ether, decyl glycidyl ether, dodecyl glycidyl ether, p-tert-butylphenyl glycidyl ether, and o-cresyl glycidyl ether. Monoepoxy esters such as the glycidyl ester of versatic acid (commercially available as CARDURA ® E from Shell Chemical Company), or the glycidyl esters of other acids such as tertiary-nonanoic acid, tertiary-decanoic acid, tertiary-undecanoic acid, etc. are also useful. Similarly, if desired, unsaturated monoepoxy esters such as glycidyl acrylate, glycidyl methacrylate or glycidyl laurate could be used. Additionally, monoepoxidized oils can also be used.

Other useful monoepoxies include styrene oxide, cyclohexene oxide, 1,2-butene oxide, 2,3-butene oxide, 1,2-pentene oxide, 1,2-heptene oxide, 1,2-octene oxide, 1,2-nonene oxide, 1,2-decene oxide, and the like.

It is only necessary that the monoepoxide compounds have a sufficiently low volatility to remain in the coating composition under the applicable conditions of cure.

Polyepoxides are especially preferred in the reactive coatings of this invention. Especially preferred as the poly-functional epoxy compounds, due to their reactivity and durability, are the polyepoxy-functional cycloaliphatic epoxies. Preferably, the cycloaliphatic epoxies will have a number average molecular weight less than about 2,000 to minimize the viscosity. The cycloaliphatic epoxies are conveniently prepared by methods well known in the art such as epoxidation of dienes or polyenes, or the epoxidation of unsaturated esters by reaction with a peracid such as peracetic and/or performic acid.

Commercial examples of representative preferred cycloaliphatic epoxies include 3,4-epoxycyclohexylmethyl 3,4-epoxycyclohexane carboxylate (e.g. "ERL-4221" from Union Carbide Corp.); bis(3,4-epoxycyclohexylmethyl)adipate (e.g. "ERL-4299" from Union Carbide Corporation); 3,4-epoxy-6-methylcyclohexylmethyl 3,4-epoxy-6-methylcyclohexane carboxylate (e.g. "ERL-4201" from Union Carbide Corp. ); bis(3,4-epoxy-6-methylcyclohexylmethyl)adipate (e.g. "ERL-4289" from Union Carbide Corp.); bis(2,3-epoxycyclopentyl) ether (e.g. "ERL-0400" from Union Carbide Corp.); dipentene dioxide (e.g. "ERL-4269" from Union Carbide Corp.); 2-(3,4-epoxycyclohexyl-5, 5-spiro-3,4-epoxy) cyclohexane-metadioxane (e.g. "ERL-4234" from Union Carbide Corp.). Other commercially available cycloaliphatic epoxies are available from Ciba-Geigy Corporation such as CY 192, a cycloaliphatic diglycidyl ester epoxy resin having an epoxy equivalent weight of about 154. The manufacture of representative cycloaliphatic epoxies is taught in various patents including U.S. Pat. Nos. 2,884,408, 3,027,357 and 3,247,144.

Other polyepoxides potentially useful in the practices of this invention include aliphatic and aromatic polyepoxies, such as those prepared by the reaction of an aliphatic polyol or poly hydric phenol and an epihalohydrin. Other useful epoxies include epoxidized oils and epoxyfunctional copolymers such as acrylic polymers derived from ethylenically unsaturated epoxyfunctional monomers such as glycidyl acrylate or glycidyl methacrylate in combination with other copolymerizable monomers such as those listed in 2.A. 5 above.

4. HYDROXY-FUNCTIONAL COMPOUNDS

The hydroxy-functional compounds which are useful in combination with the anhydride-functional polymers to prepare curable compositions in the practice of this invention should have an average of at least two hydroxyl groups per molecule. Although low molecular weight diols and polyols such as propylene glycol, 1,6 hexanediol, triethanol amine and pentaerythritol can be utilized in the practice of this invention, it is especially preferred to utilize polymeric hydroxy-functional compounds such as polyethers, poly esters, acrylics, polyurethanes, polycaprolactones, etc.

Preferably the hydroxy-functional polymer will have a number average molecular weight of at least about 400. Typical number average molecular weights will range from about 400 to about 30,000, and especially 1,000 to about 15,000. In order to provide the fastest rate of reaction during cure it is preferred to utilize hydroxy-functional compounds having predominantly, and preferably all, primary hydroxy functionality.

Representative hydroxy-functional polymers are taught in Sections 2.A. 1. through 2.A.5. Especially preferred as the hydroxy-functional polymer is a hydroxy-functional polymer comprising the addition polymerization of (a) 10 to about 60 weight percent of a hydroxy-functional ethylenically unsaturated monomer and (b) 40 to about 90 weight percent of at least one ethylenically unsaturated monomer copolymerizable with the hydroxy-functional monomer.

5. AMINE-FUNCTIONAL COMPOUNDS

Amine-functional compounds which are useful in combination with the anhydride-functional polymers to prepare curable compositions in the practice of this invention should have an average of at least two primary or secondary amine groups per molecule. Polyamines can be prepared by methods well known in the art such as by the free radical polymerization of acrylic or other unsaturated monomers having primary or secondary amine functionality, or by the reaction of amines having at least two amine groups per molecule with a polycarboxylic acid to form polyamide amines, or by the reaction of primary amines with epoxy materials to produce secondary amine and hydroxyl functionality. The polyamines can be polymeric, typically having a number average molecular weight over 400, or lower molecular materials, such as piperazine, tetraethylenepentamine, 1,2-diaminopropane, 1,6-diaminohexane, etc. Also useful are the materials having a primary or secondary amine group and a hydroxyl group such as isopropanol amine, isobutanol amine, ethanol amine, etc.

The ratios of anhydride to other functional groups in the curable compositions can be widely varied within the practice of this invention as long as at least some of each group is present in the reactive composition. It is only necessary to combine the anhydride-functional polymer and other reactive materials in amounts to provide the desired degree of crosslinking upon cure. When the anhydride-functional polymer is used as one component and either a polyol or polyamine or polyepoxide is used as the only other reactive component in the curable composition, it is preferred to provide about 0.3 to about 10 hydroxyl or amine or epoxy groups for each anhydride group, and especially 1 to about 5 hydroxyl or amine or epoxy groups for each anhydride group. When the curable composition involves a combination of only the anhydride-functional polymer, an epoxide or polyepoxide, and a polyol it is preferred to provide 0.3 to about 6.0 hydroxyl groups, and about 0.3 to about 6.0 epoxy groups for each anhydride group, and especially to provide 0.5 to 2.5 hydroxyl groups and 0.5 to 2.5 epoxy groups for each anhydride group. When the curable composition involves the anhydride-functional polymer, an acid-functional compound and a polyepoxide, it is preferred to provide 0.3 to 6.0 acid groups and 0.6 to 12.0 epoxy groups for each anhydride group, and especially 2.0 to about 5.0 acid groups and 3.0 to about 8.0 epoxide groups for each anhydride group. If the reactive curable composition comprises the anhydride-functional polymer, an acid-functional compound, an epoxide or polyepoxide, and a hydroxy-functional compound, it is preferred to provide from 0.05 to about 3.0 acid groups and about 0.5 to about 4.0 epoxy groups and about 0.05 to 6.0 hydroxyl groups for each anhydride group in the reactive system. It is especially preferred to provide 1.0 to about 2.0 acid groups and 1.0 to about 3.0 epoxy groups and about 1.0 to about 4.0 hydroxyl groups for each anhydride group.

The curable compositions of this invention can be cured at temperatures ranging from about room temperature up to about 350° F. When the curable compositions are utilized as coatings, the coatings can be used as clear coatings or they may contain pigments as is well known in the art. Representative opacifying pigments include white pigments such as titanium dioxide, zinc oxide, antimony oxide, etc. and organic or inorganic chromatic pigments such as iron oxide, carbon black, phthalocyanine blue, etc. The coatings may also contain extender pigments such as calcium carbonate, clay, silica, talc, etc.

The coatings may also contain other additives such as flow agents, catalysts, diluents, solvents, ultraviolet light absorbers, etc.

It is especially preferred in the curable compositions of this invention to include a catalyst for the reaction of anhydride groups and hydroxyl groups and/or a catalyst for the reaction of epoxy and acid groups, if present in the curable composition. It is especially preferred in the practice of this invention to utilize tertiary amines and especially N-methylimidazole as a catalyst for the anhydride/hydroxyl reaction. The catalyst for the anhydride/hydroxyl reaction will typically be present at a level of at least 0.01% by weight of the anhydride compound and preferably 1.0 to about 5.0%.

Tertiary amines, secondary amines such as ethyl imidazole, quaternary ammonium salts, nucleophilic catalysts, such as lithium iodide, phosphonium salts, and phosphines such as triphenyl phosphine are especially useful as catalysts for epoxy/acid reactions. The catalyst for the epoxy/acid reaction will typically be present at a level of at least 0.01% by weight of the total acid-functional compound and epoxy-functional compound and will be present at 0.1 to about 3.0%.

Since the curable compositions of this invention are typically provided as multi-package systems which must be mixed together prior to use, the pigments, catalysts and other additives can be conveniently added to any or all of the appropriate individual packages.

The coatings of this invention may typically be applied to any substrate such metal, plastic, wood, glass, synthetic fibers, etc. by brushing, dipping, roll coating, flow coating, spraying or other method conventionally employed in the coating industry.

One preferred application of the curable coatings of this invention relates to their use as clearcoats and/or basecoats in clearcoat/basecoat formulations.

Clearcoat/basecoat systems are well known, especially in the automobile industry where it is especially useful to apply a pigmented basecoat, which may contain metallic pigments, to a substrate and allow it to form a polymer film followed by the application of a clearcoat which will not mix with or have any appreciable solvent attack upon the previously applied basecoat. Typically, at least some of the solvent will be allowed to evaporate from the basecoat prior to the application of the clearcoat. In some applications the basecoat may even be allowed to cure, at least partially, prior to application of the clearcoat. The basecoat composition may be any of the polymers known to be useful in coating compositions including the reactive compositions of this invention.

One useful polymer basecoat includes the acrylic addition polymers, particularly polymers or copolymers of one or more alkyl esters of acrylic acid or methacrylic acid, optionally together with one or more other ethylenically unsaturated monomers. These polymers may be of either the thermoplastic type or the thermosetting, crosslinking type which contain hydroxyl or amine or other reactive functionality which can be crosslinked. Suitable acrylic esters for either type of polymer include methyl methacrylate, ethyl methacrylate, propyl methacrylate, butyl methacrylate, ethyl acrylate, butyl acrylate, vinyl acetate, acrylonitrile, acrylamide, etc. Where the polymers are required to be of the crosslinking type, suitable functional monomers which can be used in addition to those already mentioned include acrylic or methacrylic acid, hydroxy ethyl acrylate, 2-hydroxy propyl methacrylate, glycidyl acrylate, tertiary-butyl amino ethyl methacrylate, etc. The basecoat composition may, in such a case, also contain a crosslinking agent such as a carbodiimide, a polyanhydride, a polyisocyanate a polyepoxide, or a nitrogen resin such as a condensate of an aldehyde such as formaldehyde with a nitrogenous compound such as urea, melamine or benzoguanamine or a lower alkyl ether of such a condensate. Other polymers useful in the basecoat composition include vinyl copolymers such as copolymers of vinyl esters of inorganic or organic acids, such as vinyl chloride, vinyl acetate, vinyl propionate, etc., which copolymers may optionally be partially hydrolyzed so as to introduce vinyl alcohol units.

Other polymers useful in the manufacture of the basecoat include alkyd resins or polyesters which can be prepared in a known manner by the condensation of polyhydric alcohols and polycarboxylic acids, with or without the inclusion of natural drying oil fatty acids as described elsewhere in this specification. The polyesters or alkyds may contain a proportion of free hydroxyl and/or carboxyl groups which are available for reaction, if desired with suitable crosslinking agents as discussed above.

If desired, the basecoat composition may also contain waxes, rheology modifiers, cellulose esters, or other additives to alter the appearance, drying or viscosity characteristics of the basecoat.

Typically, the basecoat will include pigments conventionally used for coating compositions and after being applied to a substrate, which may or may not previously have been primed, the basecoat will normally be allowed sufficient time to form a wet polymer film which will not be lifted during the application of the clearcoat. The clearcoat is then applied to the surface of the basecoat, and the system can be allowed to dry or, if desired, can be force dried by baking the coated substrate at temperatures typically ranging up to about 250° F.

Typically, the clearcoat may contain ultraviolet light absorbers or stabilizers, such as hindered phenols or hindered amines at a level ranging up to about 6% by weight of the vehicle solids. The clearcoat can be applied by any application method known in the art, but preferably will be spray applied. If desired, multiple layers of basecoat and/or clearcoat can be applied. Typically, both the basecoat and the clearcoat will each be applied to give a dry film thickness of about 0.01 to about 6.0, and especially about 0.5 to about 3.0 mils.

The following examples have been selected to illustrate specific embodiments and practices of advantage to a more complete understanding of the invention. Unless otherwise stated, "parts" means parts-by-weight and "percent" is percent-by-weight. Number average molecular weight was determined by GPC relative to polystyrene standard.

Examples A–F show the preparation of precursor materials to the novel anhydride-functional monomers. Examples 1–3 show the preparation of selected anhydride-functional monomers and Example 4 shows the production of polymers incorporating those anhydride monomers.

The starting raw materials utilized in these examples are commercially available. The vinyl benzyl chloride is a 70/30 meta/para isomer commercially available from Dow Chemical Company. The sodium metal, diethyl malonate, ethyl chloroacetate, acetic anhydride, butylated hydroxy toluene, and, unless otherwise indicated, the triethyl-1,1,2-ethanetricarboxylate, were obtained from Aldrich Chemical Company. The absolute ethanol was obtained from USI-Quantum Chemical Company.

EXAMPLE A

Triethyl-1,1,2-ethane Tricarboxylate

A solution of sodium ethoxide in ethanol was prepared by slowly adding 559.4 g sodium metal into 7890 g of absolute ethanol. Next, 3891.9 g of diethyl malonate was added to the ethanol solution over 45 minutes at an initial temperature of 25° C. The mixture was homogenized by heating at 50° C. for 40 minutes. Next, 3000 g ethyl chloroacetate was slowly added over approximately 90 minutes, while the reaction mixture was maintained at 40° C. to 50° C. with occasional warming. The mixture was then heated at reflux for 2 hours, then cooled to room temperature.

The mixture was worked-up by stripping off approximately two-thirds of the ethanol (~750–800 ml). The residue was then washed with water and extracted with toluene. The toluene solution was dried over magnesium sulfate, followed by removal of the toluene to give a dark red residue. The product residue was distilled under reduced pressure to give 3252 g (approximately 54.3% yield) of triethyl-1,1,2-ethane tricarboxylate in ~97% purity.

EXAMPLE B

Triethyl 1-($\frac{3}{4}$-Vinyl Benzyl)-1,1,2-ethane Tricarboxylate

An ethanol solution of sodium ethoxide was prepared by adding 283 g of sodium metal over 8 hours to 6404 g of ethanol (maximum temperature 60° C.). Triethyl-1,1,2-ethane tricarboxylate (Example A, 3156.9 g) was then added over 20 minutes to the ethanol solution (maximum temperature 30° C.). The mixture was then heated at reflux for 5–10 minutes, then cooled to 25° C. Next, 1816.3 g of vinyl benzyl chloride was added over 40 minutes, while keeping the temperature under 35° C. A small amount of butylated hydroxy toluene inhibitor was added. The mixture was heated at reflux for 2 hours and 20 minutes and then allowed to cool to room temperature.

The reaction mixture was neutralized (pH ~7) with glacial acetic acid, and approximately two-thirds of the ethanol was stripped off under reduced pressure. Sodium chloride was filtered off. The unpurified styryl methylene triester/ethanol solution (63.6% NVM in ethanol) was then utilized to produce the corresponding tricarboxylic acid as shown in Example E.

EXAMPLE C

Triethyl 1 ($\frac{3}{4}$-Vinyl Benzyl)-1,1,2-ethane Tricarboxylate

A sodium ethoxide/ethanol solution was prepared by slowly adding 16.02 g of sodium metal to 365 g of absolute ethanol with slow stirring. The mixture was then heated at reflux for 5–10 minutes. Triethyl-1,1,2-ethane tricarboxylate (180 g from Aldrich Chemical Company) was added over 20 minutes to the mixture at room temperature. The mixture was heated at reflux for 5–10 minutes, then cooled to 25° C. Next, 112.9 g of vinyl benzyl chloride was added over 20 minutes (maximum temperature of the reaction mixture was 45° C.). A small amount of butylated hydroxy toluene inhibitor was added. The mixture was heated to reflux for 2 hours, then cooled to room temperature.

The reaction mixture was neutralized (pH ~7) with glacial acetic acid. About two-thirds of the ethanol was stripped off under reduced pressure. Six hundred sixty-five milliliters of deionized water was added and the product was extracted with toluene. The combined toluene extracts were dried over sodium sulfate. Removing the volatiles with rotary evaporation produced 255.2 g of triethyl-1-($\frac{3}{4}$-vinyl benzyl)-1,1,2-ethane tricarboxylate as a yellow liquid in an isolated yield of 96% of theory. NMR and infrared spectral data continued the structure of the tricarboxylate product.

EXAMPLE D 1-($\frac{3}{4}$-Vinyl Benzyl)-1,1,2-ethane Tricarboxylic Acid

An aqueous/ethanolic potassium hydroxide solution was prepared by slowly mixing 2805 ml of absolute ethanol and 147.5 ml of deionized water. A small amount of butylated hydroxy toluene inhibitor was added. Potassium hydroxide (363 g) was added slowly keeping the temperature below reflux. The mixture was then cooled to 30° C. and 240 g, (approximately 0.662 mol) of the crude product of the vinyl benzyl triester of Example C. was quickly added. The mixture rapidly turned cloudy and then became homogeneous upon heating to reflux. An additional small amount of butylated hydroxy toluene inhibitor was again added and reflux was continued for 4 hours. The precipitate laden mixture was then allowed to cool to room temperature. The tricarboxylate salt was collected by suction filtration, then dissolved in deionized water (800 ml) and neutralized with dilute aqueous hydrochloric acid (5:1 conc. HCl/H$_2$O vol. ratio) to a pH<2. Two additions of approximately 3000 ml each of anhydrous acetone was added to the acidified solution and the potassium chloride precipitate was filtered off. The acetone was then stripped off and the process was then repeated. The remaining volatiles were then removed under reduced pressure to give an isolated yield of 113.1 g (74.4%) of an off white solid (mp 112.5° C. to 125° C. decomposed). NMR, infrared and acid dissociation constants data were used to characterize the tricarboxylic acid product. In water, aqueous potassium hydroxide titration identified the Pka's of the three carboxylic acid groups as 2.60; 4.59 and 8.06.

EXAMPLE E 1-($\frac{3}{4}$-Vinyl Benzyl)-1,1,2-ethane Tricarboxylic Acid

An aqueous potassium hydroxide solution (6126 g, 109.2 mol of potassium hydroxide in 2490 g of water) was slowly added to 6375 g (11.17 mol) of the unpurified vinyl benzyl triester/ethanol solution of Example B, (36.47% NVM) containing a small amount of butylated hydroxy toluene inhibitor, while keeping the exothermic reaction below reflux. An additional small amount of butylated hydroxy toluene was again added. The mixture was then heated to reflux for 4 hours, and cooled to room temperature. The precipitated solid tricarboxylate salt was collected by filtration. Additional ethanol (12000 g) and then propanol (12000 g) were used to precipitate out the remaining salt which was collected by filtration.

A dispersion of the tricarboxylate salt was made in anhydrous acetone. The salt was neutralized by acidifying the mixture with a concentrated hydrochloric acid (HCl)/water solution (5:1 volume ratio) to a pH of <2. The acetone, aqueous HCl solution was then treated with a 2:1 hexane/toluene mixture. Stripping volatiles from the residual solution yielded 2777 g of an orange solid crude product. NMR and infrared spectral data confirmed the structure as the desired tricarboxylate. The product also contained some neutralized potassium carboxylate salt.

EXAMPLE F

2-($\frac{3}{4}$-Vinyl Benzyl) Succinic Acid

A flask containing 5.0 g (0.018 mol) of the vinyl benzyl ethane triacid (from Example D) and a small amount of butylated hydroxy toluene inhibitor was evacuated and filled with nitrogen three times. Then the material was heated to 120° C. to 135° C. Gas evolution began on melting and continued briskly for about 2.5 hours, after which the product was cooled to room temperature. Acetone (10 times reaction mixture volume) was added and the mixture stirred. Insoluble polymer was filtered off and the volatiles were then stripped away under reduced pressure to give 3.49 g of a brown, viscous, oily diacid (82.9% isolated yield) which did not crystallize. NMR and infrared spectral data confirmed the structure of the product as the desired 2-($\frac{3}{4}$vinyl benzyl) succinic acid.

EXAMPLE 1

2-($\frac{3}{4}$-Vinyl Benzyl) Succinic Anhydride

A mixture of 5 g (0.018 mol) of the vinyl benzyl triacid of Example E, 10 g (0.098 mol) of acetic anhydride and a small amount of butylated hydroxy toluene inhibitor was prepared. Gas evolution began at room temperature and the mixture was heated to a temperature of 100 ° C. to 103 ° C. in a paraffin wax bath and maintained at that temperature for 2–2.5 hours at which point the reaction mixture was allowed to cool to room temperature. Volatiles were stripped from the mixture providing 2.72 g (63.4% yield) of a brown viscous oil which was confirmed by infrared and NMR analyses as the desired 2-($\frac{3}{4}$-vinyl benzyl) succinic anhydride.

EXAMPLE 2

2-($\frac{3}{4}$-Vinyl Benzyl) Succinic Anhydride

A mixture of 500 g (1.8 mol) of the vinyl benzyl triacid of Example E), 211 g (2.07 mol) of acetic anhydride and a small amount of butylated hydroxy toluene inhibitor was prepared. Gas evolution occurred at room temperature. The reaction mixture was then maintained at a temperature of 100° C. to 103 ° C. for 2–2.5 hours. After gas evolution ceased, the reaction mixture was cooled to room temperature. Methylene chloride was added in the amount of 3–4 times the reaction mixture volume and the mixture stirred. Insoluble polymer was filtered away using suction. Volatiles were then stripped from the filtrate leaving a brown viscous oil. The viscous monomer liquid (infrared revealed high carboxylic acid content) was retreated with methylene chloride (3.5 times the reaction mixture volume) and the monomer containing solution was decanted off and the volatiles were removed under reduced pressure. The brown residue was reacted with 366 g (3.58 mol) of acetic anhydride at conditions described in Example 1 above. The same work-up as in Example 1 afforded 196.7 g (50.6% of theory) of a brown viscous liquid which predominately crystallized into a yellow solid/liquid substance. NMR and infrared spectral data identified the product as the desired 2-($\frac{3}{4}$-vinyl benzyl) succinic anhydride.

EXAMPLE 3

2-($\frac{3}{4}$-Vinyl Benzyl) Succinic Anhydride

A mixture of 3.49 g (0.0149 mol) of the vinyl benzyl succinic acid of Example F, 4.04 g (3.73 ml, 0.0396 mol) of acetic anhydride and a small amount of butylated hydroxy toluene inhibitor was prepared. The reaction mixture was stirred and heated to 100° C. A temperature of 100° C. to 103° C. was maintained for 1.5 hours. After cooling the reaction mixture to room temperature, acetone (10 times the reaction mixture volume) was added. Insoluble polymer was removed by filtration. Volatiles were then stripped from the filtrate leaving 3.11 g (96.6% isolated yield) of a brown viscous oil which was identified by NMR and infrared spectral data as the desired 2-($\frac{3}{4}$vinyl benzyl) succinic anhydride.

EXAMPLE 4

Anhydride Monomer/Ethyl Acrylate/Methyl Methacrylate Copolymer

A monomer/initiator mixture composed of a filtered solution of 159.02 g (0.735 mol) of the anhydride monomer of Example 2, 178.2 g (1.78 mol) of ethyl acrylate, 38.8 g (0.387 mol) of methyl methacrylate, 77.6 g of methyl isobutyl ketone and 33.8 g (0.176 mol) of Vazo 67 (Trademark for E. I. duPont initiator believed to be 2,2'-azobis(2-methylbutyronitrile)) was prepared and added to a heated solution (93° C.) of 310.6 g of methyl isobutyl ketone under a nitrogen sparge over a 2 hour period. After holding at the reaction temperature for 15 minutes, an additional 0.39 g of Vazo 67 was added and the mixture was held at the reaction temperature for an additional 20 minutes. The polymer mixture was diluted with 1.5 times its volume with methyl isobutyl ketone and then precipitated into 7.5 liters of rapidly stirred hexane. The hexane was decanted and the resultant wet resin was dried overnight at 60° C. under aspirator pressure. A yield of 344 g (91.5% of theory) of an acrylic copolymer was obtained. The resin was then reduced to approximately 65% weight solids (NVM) in methyl isobutyl ketone. The polymer had a number average molecular weight (Mn) of 2889, a polydispersity of 2.2 and an anhydride equivalent weight of 575. The resin solution had a Brookfield viscosity of 10.9 and a Gardner-Holt viscosity of V. A Tg value of 30° C. was obtained by differential scanning calorimetry. The composition of the polymer, in parts by weight of the anhydride monomer of Example 2/ethyl acrylate/methyl methacrylate was 42.3/47.4/10.3.

EXAMPLE 5

Preparation of Clear Coating

A curable, two-package, clear coating having a ratio of anhydride groups/hydroxy groups/epoxy groups of 2/1/2 was prepared according to the following recipes:

| Raw Material | Parts-By-Weight |
| --- | --- |
| Package 1 | |
| Anhydride-Functional Polymer of Example 4 | 393.48 |
| Package 2 | |
| Hydroxy-Functional Acrylic Resin[1] | 151.24 |
| ERL 4229[2] | 88.47 |
| Solvent Blend[3] | 120.29 |
| Byk 300[4] | 2.5 |
| 20% Tinuvin 328[5] in Toluene | 28.97 |
| Tinuvin 292[6] | 3.36 |
| 20% N-methylimidazole in Methyl Isobutyl Ketone | 44.55 |

[1]Copolymer of hydroxy ehtyl methacrylate/hydroxy ethyl acrylate/styrene/methyl methacrylate/butyl methacrylate/butyl acrylate/ethyl hexyl acrylate in a weight ratio of 20/11.2/16/14/14/12.8/16/6 extended with two moles of caprolactone per mole of hydroxyl and reduced to 80% NVM. The polymer had a hydroxyl equivalent weight of 544.3, a number average molecular weight (GPC) of 3200, and a weight per gallon of 8.73.
[2]Trademark of Union Carbide for bis(3,4-epoxycyclohexylmethyl)adipate.
[3]n-butyl acetate/propylene glycol monomethyl ether acetate/ethyl 3-ethoxypropionate/dimethyl glutarate in a 65.5/10.6/16.7/7.2 weight ratio.
[4]Flow control agent sold by Byk-Malinkrodt.
[5]Trademark of Ciba-Geigy for 2-(2-hydroxy-3,5-ditertiary amyl-phenol)-2H-benzotriaozle.
[6]Trademark of Ciba-Geigy for di[4(2,2,6,6-tetramethyl piperdinyl)]sebacate light stabilizer.

Packages 1 and 2 were mixed together and this coating was spray applied at a VOC (volatile organic content) of 3.5 lbs/gallon over a basecoat/primer system coated on Bonderite®-1000 panels (iron phosphate treatment on cold rolled steel). The basecoat/primer system consisted of basecoat (Ultra Base 7® Metallic Basecoat, commercially available from The Sherwin-Williams Company) and a primer (Q-Seal® primer P1A60 commercially available from The Sherwin-Williams Company). The dry film thicknesses were approximately one mil for primer, one mil for basecoat and two mils for clear coat. The coating system was allowed to cure twenty-four (24) hours under ambient conditions prior to initial testing. The cured panels exhibited a 20° gloss of 79, a konig pendulum hardness (KPH) of 24 after four (4) weeks, and excellent resistance to methyl ethyl ketone and gasohol after four (4) days of air dry cure.

EXAMPLE 6

Preparation of Colored Basecoat

A curable, two-package, pigmented coating, suitable as a pigmented topcoat or as a basecoat, and having one anhydride group per two hydroxyl groups was prepared according to the following recipes:

| Raw Materials | Parts-By-Weight |
| --- | --- |
| Package 1 | |
| Anhydride-Functional Polymer of Example 4 | 39.84 |
| Package 2 | |
| Hydroxy-Functional Resin[7] | 31.14 |
| Non-Leafing Aluminum Paste Reynolds 5-10 AV | 27.32 |
| Methyl Ethyl Ketone | 12.9 |
| Toluene | 12.9 |
| N-methyl imidazole | 0.9 |

[7]Obtained by reacting 24.0 parts trimethylol ethane and 184.7 parts caprolactone to provide essentially 100% NVM polyester polyvol having an equivalent weight of 345, and a number average molecular weight (GPC) of approximately 1300.

Packages 1 and 2 were mixed together and this coating formulation was spray applied over Bonderite-1000 steel panels which had been primed with JET SEAL® E2A28 primer (commercially available from The Sherwin-Williams Company). The basecoat was subsequently clear coated with ULTRABASE 7® acrylic-/urethane clearcoat T1C650 (commercially available from The Sherwin-Williams Company) to provide dry film thicknesses of approximately one mil primer, two mils basecoat and two mils clearcoat. The coating system gave excellent metal brightness.

Other reactive systems, such as the combination of a poly epoxy-functional material, an acid-functional material and the anhydride-functional polymer of this invention are also practical, and could, optionally, also incorporate hydroxy-functional materials as well.

While this invention has been described by a specific number of embodiments, that other variations and modifications may be made without departing from the spirit and scope of the invention as set forth in the appended claims.

The entire disclosure of all applications, patents and publications cited herein are hereby incorporated by reference.

The invention claimed is:

1. An anhydride-functional monomer having the structure:

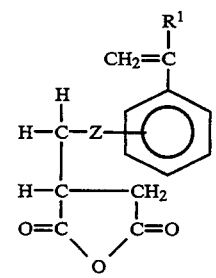

wherein $R^1$ is hydrogen or methyl; and Z is nothing or is a divalent radical having 1 to about 20 carbon atoms.
2. The monomer of claim 1 wherein $R^1$ is hydrogen.
3. The monomer of claim 1 wherein $R^1$ is methyl.
4. The monomer of claim 2 wherein Z is nothing.
5. The monomer of claim 3 wherein Z is nothing.
6. The monomer of claim 1 wherein Z is a divalent polymethylene chain $—(—CH_2—)_n—$ wherein n is 1 to 20.

* * * * *